United States Patent [19]

Armentrout et al.

[11] 4,296,862
[45] Oct. 27, 1981

[54] DEVIOUS PATH BACTERIAL BARRIER

[76] Inventors: James L. Armentrout, 21 Barlovento Ct., Newport Beach, Calif. 92663; George H. Schneider, 22475 Overlake Dr., El Toro, Calif. 92630

[21] Appl. No.: 70,134

[22] Filed: Aug. 27, 1979

[51] Int. Cl.³ .................. B65D 81/24; B65D 33/16; B65D 51/16
[52] U.S. Cl. .................. 206/439; 206/484.1; 119/1; 220/374; 229/62.5
[58] Field of Search .................. 206/439, 484.1, 563, 206/834, 813; 119/1; 43/121, 123; 220/374; 229/62.5; 426/126, 118; 435/261, 311, 287, 800

[56] References Cited

U.S. PATENT DOCUMENTS

| | | | |
|---|---|---|---|
| 2,361,344 | 10/1944 | Yates | 206/813 |
| 2,870,954 | 1/1959 | Kuwesza | 426/126 |
| 3,260,236 | 7/1966 | Jones | 119/1 |
| 3,459,324 | 8/1969 | Miller | 220/374 |
| 3,697,223 | 10/1972 | Koualcik et al. | 206/563 |
| 4,124,141 | 11/1978 | Armentrout et al. | 206/439 |
| 4,206,870 | 6/1980 | Devries | 426/118 |

FOREIGN PATENT DOCUMENTS 72520  6/1893  Fed. Rep. of Germany ........ 43/123

*Primary Examiner*—William T. Dixson, Jr.
*Attorney, Agent, or Firm*—Charles H. Schwartz; Ellsworth R. Roston

[57] ABSTRACT

A devious path bacterial barrier for providing an air/gas pathway to a sterile environment from an external environment, including a flat member lying within a plane and having spaced openings extending into the flat member and with one of the openings for communicating with the exterior environment and with the other of the openings for communicating with the sterile environment, a pathway extending between the openings and with the pathway extending within the flat member and along the plane of the flat member for interconnecting the openings and providing an air/gas pathway between the one opening of the flat member and the other opening, and the pathway including a plurality of bends along its length and with each bend providing an area to trap any bacteria introduced into the pathway from the exterior environment communicating with the one opening and with all the bacteria trapped at a distance along the pathway before the other opening communicating with the sterile environment.

24 Claims, 13 Drawing Figures

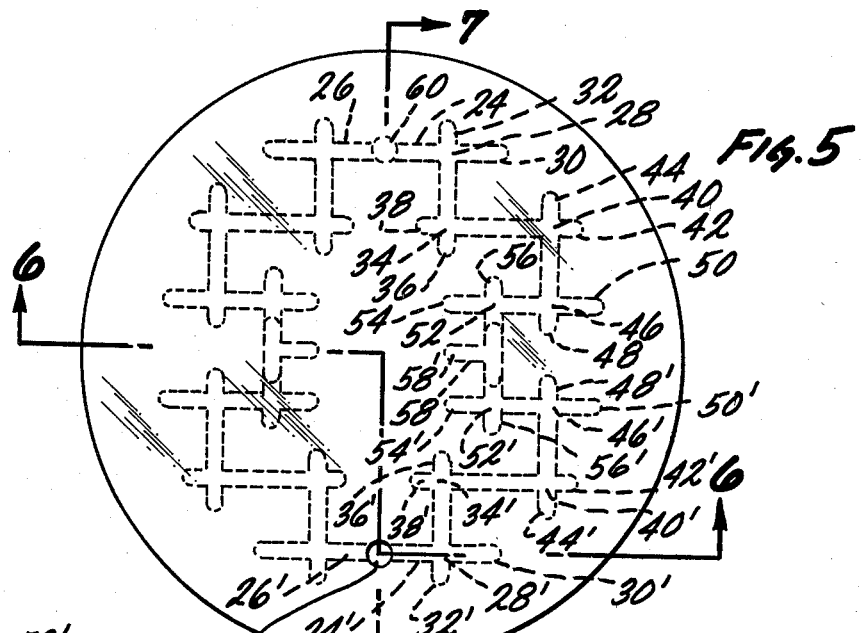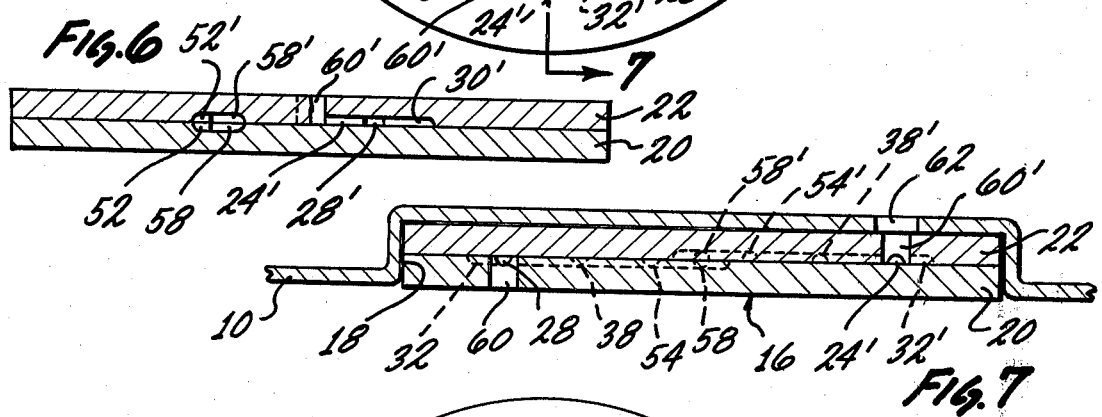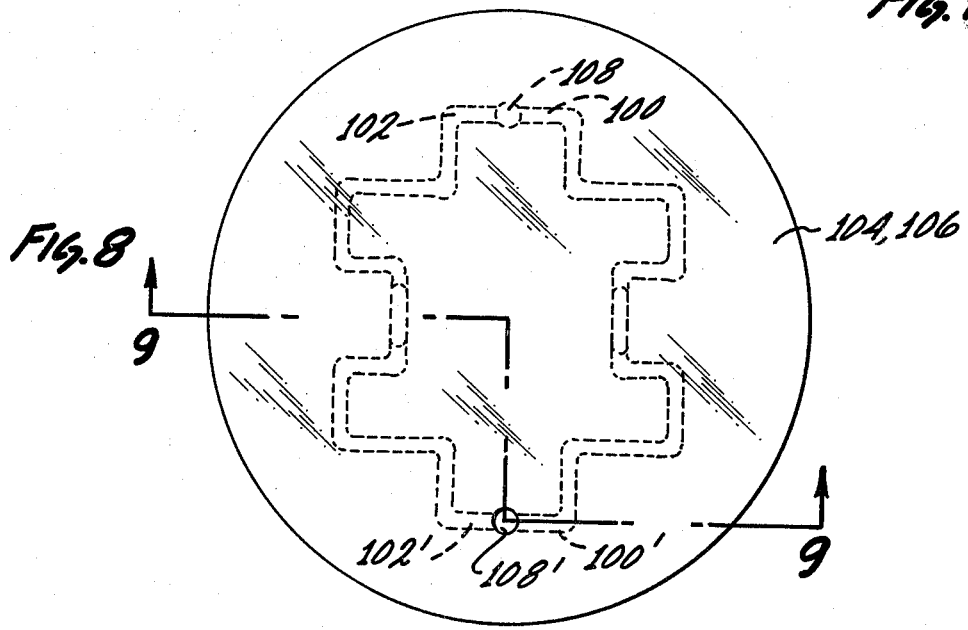

DEVIOUS PATH BACTERIAL BARRIER

The present invention is directed to a devious path bacterial barrier for use for providing and maintaining sterility within a package. Specifically, the present invention discloses structure for providing an air/gas pathway into the package and with this pathway including a bacterial barrier in the form of a devious path.

The use of sterile packages containing different types of items is currently used and, in particular, is currently used in the medical field. For example, these packages may contain medical devices such as implantable heart valves, pacemakers, mammaries, et cetera, or the package may form a medical procedure tray containing various items necessary for the procedure. These and any other devices may be enclosed in the package and the enclosed package must be capable of preventing the intrusion of bacteria which could contaminate the device within the package. The package, therefore, must maintain the sterility of the product contained within the package until the package is opened and the product removed for use.

In addition to preventing the intrusion of bacteria and thereby maintaining the sterility of the product, the package must also be capable of allowing sterilization of the product after the product is placed in the package and the package sealed. There have been numerous methods used for providing the sterilization of the product contained in the sealed package. For example, such methods of sterilization have included heat, radiation, ultraviolet light and sterilizing gas such as ethylene oxide gas or a combination of ethylene oxide gas and freon gas. The most common method of sterilization which is used is that of a sterilizing gas such as ethylene oxide since this method is economical and is less damaging to the products within the sealed package. In addition, when properly executed, the use of a sterilizing gas such as ethylene oxide is the most positive method of destroying bacteria trapped in the sealed package or on the product within the sealed package.

In order to accomplish sterilization using a sterilizing gas such as ethylene oxide, the sealed package must include an air/gas pathway into the package. Generally, a number of sealed packages, each containing a product to be sterilized, are placed in a large chamber. A vacuum, such as a vacuum of 29.5 inches of mercury, is pulled in the chamber to reduce the pressure in the chamber. As the vacuum is created in the chamber, a vacuum is also created in each package because of the air/gas pathway.

A sterilizing gas such as ethylene oxide is then injected into the chamber and because of the vacuum within the packages, the gas is drawn through the air/gas pathway into the packages and allowed to remain within the packages for a sufficient period of time to sterilize the interior of the packages. The period of time is normally governed by the product which is contained in the package and, as an example, the resident time of the sterilizing gas in the packages may vary from three hours to as long as twenty-four hours.

At the end of the sterilizing time a second vacuum is pulled in the chamber so as to remove the sterilizing gas from the chamber and from the packages through the air/gas pathways. After the sterilizing gas is removed from the chamber and the packages therein, the chamber and the packages are allowed to return to atmospheric pressure. After the chamber has returned to atmospheric pressure, the sterile packages may then be removed from the chamber.

Ideally, it would be desirable that the sterile package be completely closed in a hermetic fashion so as to prevent completely the entry of air or dust into the package that might contaminate the product and make it unsafe for medical purposes. However, as indicated above, when using a sterilizing gas, there must be a free transfer of air and gas into and out of the package during the sterilizing process. This necessitates the air/gas pathway into the package. This type of pathway is commonly called a bacterial barrier air/gas path since the pathway allows for the free passage of air or gas but provides for a barrier to bacteria.

Generally the prior art provides for an aperture in the package and with this aperture closed by the use of structures such as porous membranes made of paper, non-woven plastic sheets, cotton pledgets or other materials. All of these materials are pervious to the flow of air and gas but impervious to the passage of bacteria through the material. For example, the membrane or other bacterial barrier air/gas pathway may be provided as a label over a hole in the sterile package or may be provided as a cover member for the package or may even form one surface of the package.

Although the above types of prior art bacterial barrier air/gas pathways have been used over a long period of time, problems can occur with the prior art types of materials. For example, it is often determined that a material used to provide for the bacterial barrier air/gas pathway is allowing the passage of bacteria and the material must then be rejected. If the material were not rejected, the bacterial barrier would not function properly and a contaminated product may be used by the doctor and other medical personnel which could create serious results.

The reasons why the prior art materials may fail in preventing the passage of bacteria are many. Specifically, the material may be insufficiently porous to pass the sterilizing gas and, therefore, the product will not be properly sterilized within the package. Alternatively, the material may contain openings sufficiently large to allow the entry of bacteria into the package during shipping or storage thereby contaminating the product within the package.

Additionally, the prior art types of bacterial barriers require some sort of adhesive to adhere the material to the package. If the adhesive is not properly chosen or is improperly applied to the material forming the bacterial barrier, then either during the processing of the package or during the shipment and storage of the package, the material can separate from the package. This can produce a separation between the material and discrete portions of the package to thereby create channels into the package. These channels may of course allow the passage of bacteria into the package which, in turn, would contaminate the product contained within the package.

Another problem with the prior art bacterial barriers may occur where the product contained within the package is made of silicone, plastisols or similar materials. In such a case the product may exude sufficient oils, fillers or carriers which could then contact the bacterial barrier material and plug the porous portions of the material. This would then block the air/gas path and would prevent the sterilizing gas from producing a sterilization of the product within the package.

The present invention overcomes a number of difficulties of the prior art by providing for an air/gas path which forms a bacterial barrier through the use of a devious path. Generally, in a broad sense, the devious path bacterial barrier was discovered by Pasteur when he created his celebrated experiments to prove that the majority of disease causing bacteria were transmitted by air and dust circulating about a given area. Pasteur boiled broth in a flask with a long sinuous S-shaped neck so as to kill any bacteria in the flask. Air was able to enter the neck but any air-floating organisms settled and remained in the long sinuous S-shaped neck and the broth, therefore, remained sterile indefinitely. However, when the sinuous neck was cut off near the flask and dust and organisms could fall directly into the broth, fermentation set in within hours.

Pasteur's experiment has been recreated in laboratories innumerable times which demonstrates that a devious path may provide for a positive bacterial barrier. However, it might be difficult for a microbiologist or a biologist to accept such a devious path as a bacterial barrier for sterile packages. Generally, it would be difficult to make this acceptance since the devious path does provide an open passageway into the interior of the package and with no physical barrier between the product contained within the package and the exterior of the package. Also, it has not been until recently that studies were conducted which determined why the bacteria would remain in the sinuous devious path and would refuse to enter the interior of the package.

It was discovered in the early 1970s that bacteria in nature, but not in laboratory cultures, stick tenaciously to many surfaces ranging from the human tooth or lungs to rocks submerged in fast-moving streams. The bacteria adhere to the surface by a mass of tangled fibers of polysaccharides, or branching sugar molecules, that extend from the bacterial surface and form a felt-like glycocalyx surrounding an individual cell or colony of cells.

As indicated above, the relationship of the bacterial cell surfaces have become known only in the last decade. The main reason for this late discovery of the bacterial glycocalyx and its function was the long reliance by microbiologists in their studies of pure laboratory cultures of an individual bacterial strain. To generate and maintain a glycocalyx, a bacterial cell must expand energy, and in the environment of a pure culture, the glycocalyx is a metabolically expensive luxury conferring no selective advantages. Normally cells that fabricate these elaborate coatings are eliminated by uncoated mutants that can devote more of their energy budget to proliferation. Therefore, in nearly all instances, microbiologists have studied these naked mutants and, therefore, lacked proof that the bacteria could and would stick at the corners or in the pockets of a devious path.

The present invention, therefore, provides for a bacterial barrier air/gas path formed as a devious path from the exterior to the interior of the package. Specifically, devious paths may be formed in the plane of a flat, elongated member and with the member affixed to or forming one surface of the package and with an opening at the end of the devious path communicating with the interior of the package. In a preferred embodiment of the devious path bacterial barrier of the present invention, a pocket is formed at the end of each bend of the devious path where the pathway turns so as to form a labyrinth.

It was determined during experiments that the pockets tend to trap the bacteria and the bacteria remain permanently in these pockets. During the experiments it was also observed that the pockets closest to the exterior opening of the devious path always contained the largest amount of bacteria and as the devious path continued toward the interior of the package, each succeeding pocket along the devious path contained less and less bacteria. At some point along the devious path, no bacteria was observed in the remaining pockets and the air or gas entering the interior portions of the package was totally free of bacteria.

Although the use of the pockets facilitates the trapping of the bacteria, it is to be appreciated that a long sinuous path with a plurality of bends will also provide for a bacterial barrier. This is demonstrated by the original Pasteur experiments especially in view of the recent determinations as to why bacteria stick. The devious path bacterial barrier of the present invention may therefore be formed without the pockets and still prevent the passage of bacteria into the interior of the package.

A clearer understanding of the invention will be had with reference to the following description and drawings wherein FIG. 1 illustrates a top perspective view of a sterile package including a bacterial barrier air/gas pathway;

FIG. 5 illustrates a composite of the bottom disc and top disc forming the complete first embodiment of the devious path bacterial barrier;

FIG. 6 illustrates a cross-sectional view of the first embodiment of FIG. 5 taken along lines 6—6 of FIG. 5;

FIG. 7 illustrates a cross-sectional view of the first embodiment of FIG. 5 taken along lines 7—7 of FIG. 5 and with the devious path bacterial barrier positioned within a recess in the package wall;

FIG. 8 illustrates a second embodiment of a devious path bacterial barrier;

Figure 1:
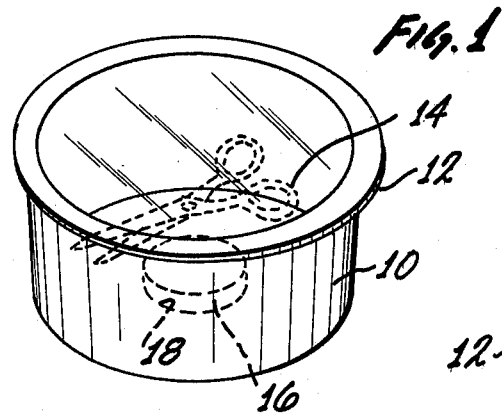

In FIG. 1, a sterile package is shown to include a body member 10 and a cover member 12. The cover member 12 may be attached to the body member 10 by any known means. For example, the cover 12 may be attached across the body 10 by heat welding, ultrasonic welding, adhesives or the cover and body may be connected by interlocking flange members. Whatever method of attachment is used, the cover member 12 is sealed across the body member 10 to provide for a sealed package which may contain a product 14 such as a medical device. The product 14, of course, if placed in the package prior to the cover member 12 being sealed across the opening of the body member 10.

In order to provide for the sterilization of the device 14 within the package, an air/gas pathway 16 is used so as to allow for the passage of a sterilizing gas such as ethylene oxide or a combination of ethylene oxide and freon. The gas pathway 16 may be disposed in a recess 18 in the bottom wall of the package but it is to be appreciated that an air/gas pathway may be disposed in or form any wall portion of the package or may be disposed in or form a portion of the cover member 12. The particular positioning of the air/gas pathway could depend on the shape and type of sterile package which is used. The air/gas pathway must, in addition to allowing for the free passage of the sterilizing gas into and out of the interior of the package, also act as a bacterial barrier to the passage of any bacteria into the interior of the package from an exterior position.

Figure 3:
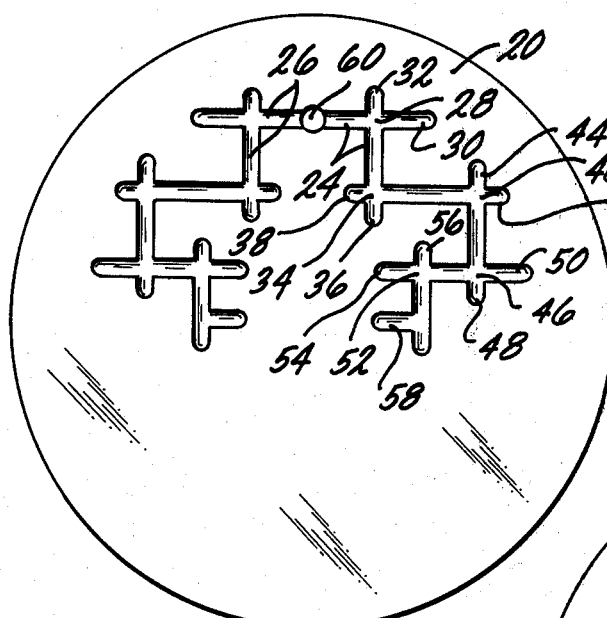
FIG. 3 illustrates a bottom disc used as part of the first embodiment of the devious path bacterial barrier.
Figure 4:
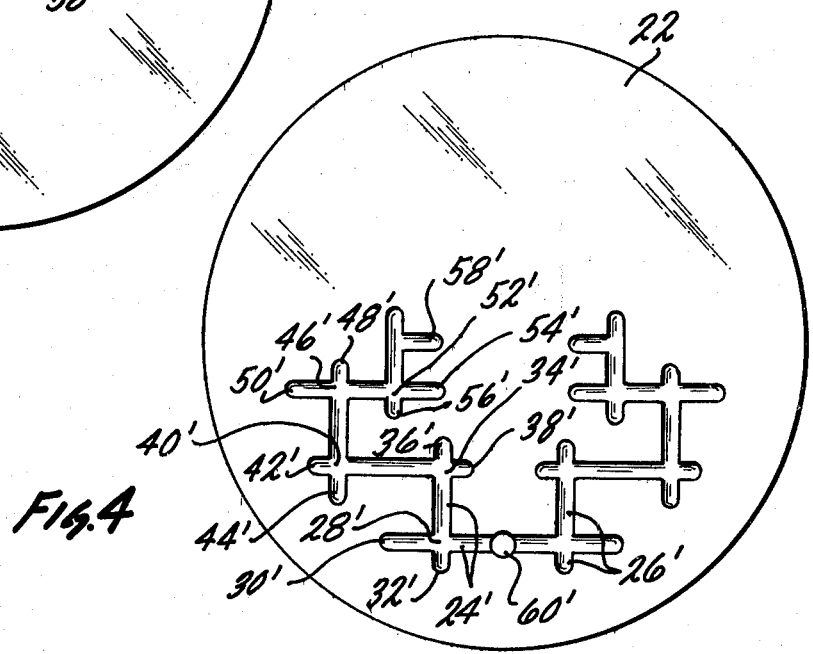
FIG. 4 illustrates a top disc used as part of the first embodiment of the present invention.
Figure 9:
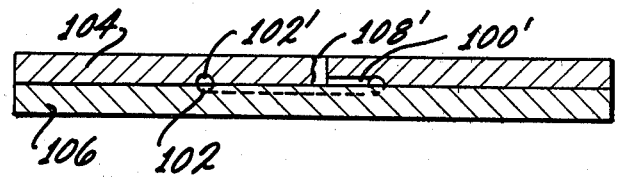
FIG. 9 is a cross-sectional view of the second embodiment taken along lines 9—9 of FIG. 8.
Figure 11:
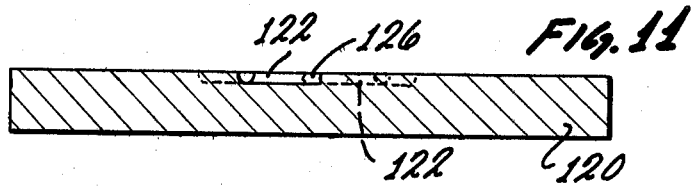
FIG. 11 is a cross-sectional view taken along lines 11—11 of FIG. 10.
Figure 12:
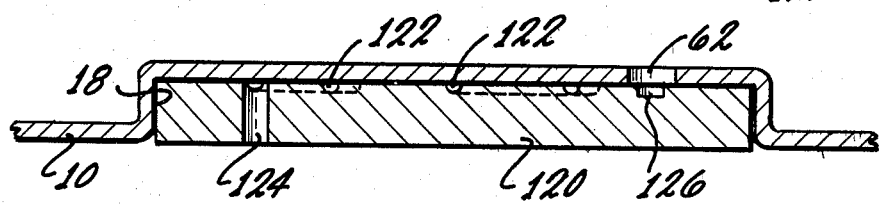
FIG. 12 is a cross-sectional view of the third embodiment of FIG. 10 taken along lines 12—12 of FIG. 10 and with the devious path bacterial barrier positioned within a recess in the package walls.
Figure 10:
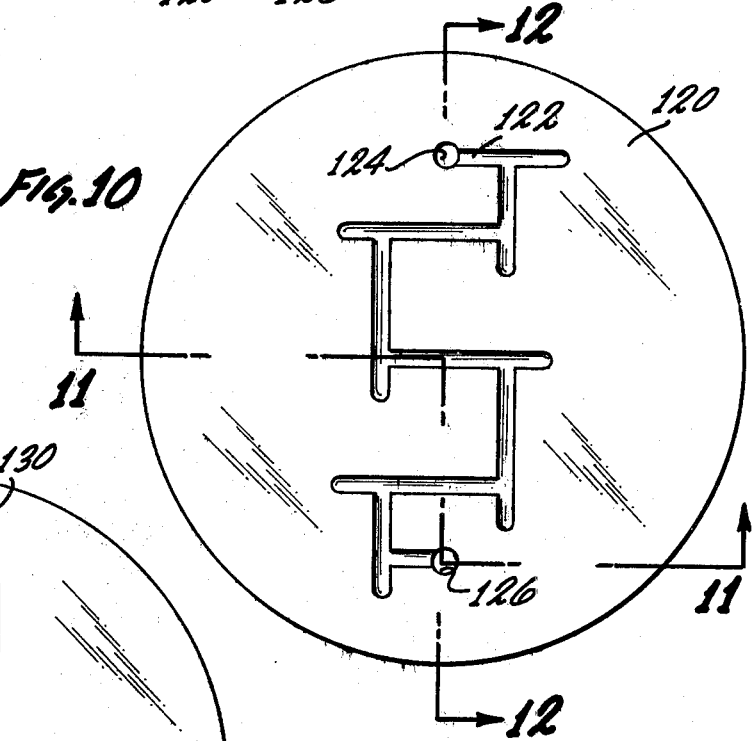
FIG. 10 illustrates a third embodiment of a devious path bacterial barrier.
Figure 13:
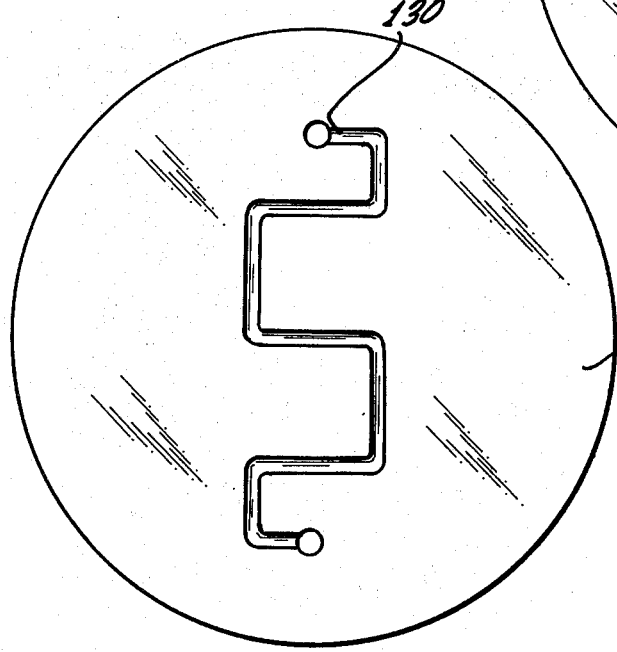
FIG. 13 is a fourth embodiment of a devious path bacterial barrier.

In a first preferred embodiment of the invention, the devious path bacterial barrier is constructed from a pair of disc members as shown by the bottom disc 20 in FIG. 3 and top disc 22 in FIG. 4. Actually, the bottom and top discs 20 and 22 may be substantially identical to each other. Each disc may include an identical devious path in one surface and with one disc rotated relative to the other so that each disc serves as a cover for the other. The bottom disc 20 includes a devious path formed as two branching paths 24 and 26 and with each branching path formed as a groove extending along one surface of the disc 20.

Each branching path 24 and 26 includes a plurality of right-angle turns and with pockets formed at each right-angle turn so that the devious path resembles a labyrinth. For example, a first right-angle turn 28 in the path 24 includes pockets 30 and 32. A second right-angle turn 34 includes pockets 36 and 38. A third right-angle turn 40 includes pockets 42 and 44. A fourth right-angle turn 46 includes pockets 48 and 50. A fifth right-angle turn 52 includes pockets 54 and 56. A stub member 58 extends along the last portion of the path 24.

The path 26 has substantially identical turns and pockets as path 24. Additionally, the top disc 22 includes substantially identical devious paths designated by reference characters 24' and 26' also formed as grooves in one surface of the disc 22. The paths 24' and 26' include right-angle turns and pockets designated the same as paths 24 and 26 except with the addition of the prime "'". The paths 24 and 26 in the disc 20 each runs from an opening 60 which opening extends completely through the disc 20. The disc 22 has a similar opening 60' which extends through the disc 22'.

When the faces of the discs 24 and 22 containing the grooves are brought into contact with each other by rotating one disc relative to the other, then the portion of the face of each disc which does not contain grooves forms a cover for the grooved portion of the face of the other disc. Specifically, the faces of the two discs are adhered to each other using conventional means such as heat welding, ultrasonic welding, adhesives or any other suitable means. A continuous path is provided from the opening 60 in the disc 20 and along the grooves 24 and 26 and then along the grooves 24' and 26' to the other opening 60' in the disc 22. This can be seen with reference to the complete devious bacterial barrier shown in FIGS. 5, 6 and 7.

As can be seen in FIGS. 5, 6 and 7, the continuous channel now exists from the outside of the bottom disc 20 to the outside of the top disc 22. The opening 60 is labeled "raw air in" and the opening 60' is marked "filtered air". The channel continues through the parallel paths 24 and 26 and the parallel paths 24' and 26' through the overlapping portions of the paths. It can be seen, therefore, that there is a complete air or gas pathway from the opening 60 to the opening 60' in both directions.

As can be seen in FIG. 7, the composite structure 16 which forms the devious path bacterial barrier is positioned within the recess 18 in the wall of the body member 10. The composite structure 16 as indicated above is formed from the top and bottom discs. The composite structure is adhered within the recess 18 using any suitable means such as heat welding, ultrasonic welding, adhesives or any other suitable means. It is to be appreciated that the composite structure which forms the devious path bacterial barrier may be positioned at any wall portion of the body member 10 or the cover member 12 or may itself form the wall portion or be a cover member.

The recess portion 18 includes an opening 62 and as shown in FIG. 7 the opening 60' in the top disc is located adjacent the opening 62 so that air or gas passing into the opening 60 and through the grooves ultimately passes from the opening 60' through the opening 62 into the interior of the container. The air/gas pathway is, of course, reciprocal to allow for the complete sterlization procedure. It is to be appreciated that the opening 62 may be larger or smaller than that shown and may be as large as the diameter of the discs.

Figure 2:
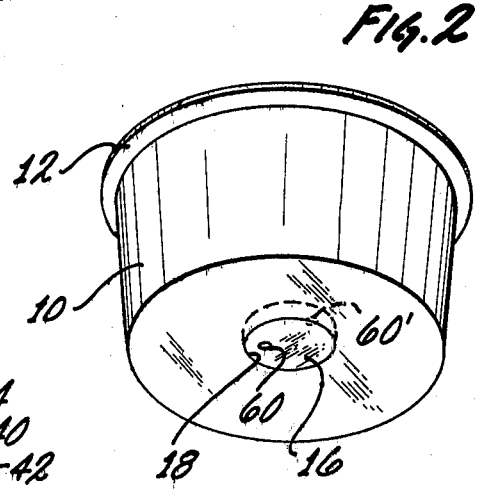
FIG. 2 illustrates a bottom perspective view of the sterile package of FIG. 1.

It can be seen that if the container is completely sealed as shown in FIGS. 1 and 2 then the only ingress or egress into and out of the container is through the various grooves described above which provide the devious path. Since all of the air or gas must pass through this devious path then, if the devious path operates to exclude bacteria, dust or other foreign matter in any air passing through the devious path, then the devious path will protect any sterile product contained in the package.

In order to determine whether the devious path operates as a bacterial barrier, a series of tests were conducted on devious path bacterial barriers including a devious path having a configuration such as that shown in the preferred embodiment of FIGS. 3 through 7. In the preferred embodiment shown in FIGS. 3 through 7, at each turn or bend in the labyrinth, a pocket was formed just prior to each turn. The particular tests determined that the devious path operates as an effective bacterial barrier and an effective bacterial dust filter for sterile packages.

The tests were designed to test the effectiveness of the devious path under stress conditions far beyond any that the packages might be exposed to under normal handling, shipping or storage. The results of the tests indicated that the devious path bacterial barrier and bacterial dust filter completely protected the inner portion of the packages against the intrusion of bacteria or dust into the interior of the packages.

In the specific tests of the preferred embodiment shown in FIGS. 3 through 7, it was determined that after the packages were first sterilized and then subjected to violent conditions tending to introduce bacteria and bacterial dust into the raw air input 60, the bacteria or dust did not penetrate through the devious path. Specifically, it was determined that the bacteria tended to accumulate in the pockets at the end of each turn and would rapidly decrease in number until a pocket was found with no bacteria and all succeeding pockets had no bacteria. In a particular example, it was found that in pocket 30 there would be a high bacterial count, in pocket 36 the bacterial count was approximately 1/10ths than that in pocket 30. The bacterial count in pocket 42 was approximately 1/100ths of that in pocket 36. In pocket 48 and all succeeding pockets the bacterial count was zero. The various turns and the pockets were therefore functioning as a progressive trap and filter thereby providing a positive bacterial barrier against the intrusion of bacteria into the packages.

As indicated above, it has been determined why the bacteria stick and upon examination of the devious path devices which have been tested under high magnification, it was revealed that the bacteria anchor themselves to smooth plastic by spinning a mat of polysaccharide fibers that can withstand very high shear forces. It was also determined that as the bacteria produced the polysaccharide mat, this mat also trapped any dust or soil particles which would normally tend to propagate the bacteria. Although the preferred embodiment of the invention includes the pockets at the end of each bend so as to facilitate the trapping of the bacteria, it is to be appreciated that as Pasteur determined, the devious path can be formed without these pockets.

FIGS. 8 and 9 illustrate a second embodiment of the invention similar to that shown in FIGS. 3 through 7 but with grooves 100 and 102 and 100' and 102' formed in a top disc 104 and a bottom disc 106 but without pockets at the end of the turns. The remaining structure of the second embodiment is substantially similar to that of the first preferred embodiment with the openings 108 and 108' forming with the grooves a complete path from the exterior of one disc to the exterior of the other. The bacteria would tend to adhere at the corners of each turn in the grooves and would progressively decrease in number from each turn through succeeding turns. Although the air or sterilizing gas could freely pass into and out of the container to provide for sterilization, once sterilization has been accomplished, the devious path would act as a barrier to the entry of bacteria into the interior of the sealed and sterile container during normal flow of air into the container during normal handling, shipping and storage.

FIGS. 10, 11 and 12 illustrate a third embodiment of the devious path bacterial barrier of the present invention using a single flat member in combination with the container wall for forming the labyrinth channel. Specifically, as shown in FIGS. 10 through 12, a flat member 120 has formed in one surface an elongated groove 122. This groove 122 extends in a labyrinth fashion and includes pocket members at each turn. These pocket members extend in only one direction since the devious path bacterial barrier of FIGS. 10 through 12 must be positioned within a recess in the container wall with a particular orientation.

Specifically, an exterior opening 124 extends completely through the flat member 120 whereas an interior open portion 126 does not extend through the flat member 120 and is essentially a continuation of the groove 122. The open portion 126 is adjacent the opening 62 in the recess 18 of the container portion 10. This structure is similar to that shown in FIG. 7. The air/gas channel is formed by the groove 122 as covered by the surface of the recess 18 when the disc 120 is adhered within the recess 18.

With the preferred embodiment shown in FIGS. 3 through 7, and since the top and bottom discs are identical, the pockets are provided in both directions at each bend. In this way, the composite device 16 is universal and either end or either side of the composite device 16 can be positioned within the recess. This, of course, is an aid in insuring that the devious path device 16 is properly positioned within the recess portion of the container. With the devious path member shown in FIGS. 10 through 12, the disc member 120 must be properly positioned within the recess portion of the container. The embodiment shown in FIGS. 10 and 12 does have the advantage of being simpler in construction and having less steps in the manufacture and installation as compared with the devious path structure shown in FIGS. 3 through 7.

A fourth embodiment of the invention is shown in FIG. 13 and includes the disc 120 having a devious path 130 without pockets at each end of the bend. The remaining structure is similar to that shown in FIGS. 10 through 12.

The present invention, therefore, is directed to a highly efficient bacterial barrier for sterile packages and operates with great precision in preventing the intrusion of bacteria or bacteria carrying dust into the interior portions of the sterile packages. The present invention provides for a devious path bacterial barrier including a flat elongated member which may be formed as a disc or may have any other configuration and with a labyrinth channel extending along the member from one portion of the member to another portion. An opening is provided from one side of the flat member to the channel and with the other end of the channel communicating wit an opening into the interior of the package. An air/gas pathway is then formed which extends along the elongated channel and with the channel including a plurality of bends and with the bacteria or bacteria carrying dust captured in progressively greater quantities at each bend in the path from the exterior to the interior of the package. In practice, the number of bacteria is reduced significantly at each bend and with all of the bacteria eliminated prior to the interior end portion of the channel.

In a preferred embodiment of the invention, the devious path is formed by substantially identical disc members each having grooved portions in one surface and with the discs adhered to each other and with at least a portion of the grooved portions of each disc overlying each other so as to form a continuous channel initially lying within one disc and then crossing over to the other disc. Openings are provided at the ends of the channel to provide for communication to an opening into the interior of the package and an opening to the exterior. In the preferred embodiment, a pocket is formed at each bend of the channel to aid in trapping the foreign materials such as the bacteria or the bacteria carrying dust. Other embodiments of the invention do not include the use of the pockets and may provide for the channel formed in a single elongated member.

Although the invention has been described with reference to particular embodiments, it is to be appreciated that various adaptations and modifications may be made and the invention is only to be limited by the appended claims.

We claim:

1. A devious path bacterial barrier for providing an air/gas pathway into and out of a sealed package from an exterior environment through an aperture in one wall of the package, including
- a flat member lying within a plane and having spaced openings extending into the flat member on opposite sides of the flat member and with one of the openings for communicating with the exterior environment and with the other of the openings for overlying the aperture in the one wall of the package,
- a pathway extending between the openings of the flat member and with the pathway extending within the flat member and along the plane of the flat member for interconnecting the openings and providing an air/gas pathway for both directions of air/gas flow between the one opening of the flat member and the other opening, and
- the pathway including a plurality of bends along its length and with each bend providing an eara to trap any bacteria introduced into the pathway from the exterior environment to the one opening and with all the bacteria trapped at a distance along the pathway before the other opening.

2. The devious path bacterial barrier of claim 1 additionally including individual pockets located at at least some of the bends and with the pockets extending in at least one direction of the air/gas flow along the pathway.

3. The devious path bacterial barrier of claim 2 wherein the pockets are located at the bends in both directions of air/gas flow along the pathway.

4. The devious path bacterial barrier of claim 1 wherein the flat member is formed from two portions each having a part of the pathway formed as a groove in one surface and with the surfaces contiguous and with at least a portion of each groove overlying the other to provide a continuous pathway between the grooves in each portion.

5. The devious path bacterial barrier of claim 4 wherein the two portions including the grooves are substantially identical and with one portion rotated relative to the other to form the continuous pathway.

6. The devious path bacterial barrier of claim 1 wherein the flat member is formed from a single portion having a groove in one surface and with the surface contiguous with the wall of the package to provide the continuous pathway.

7. A devious path bacterial barrier for providing an air/gas pathway for two opposite directions of air/gas flow, including an elongated pathway for two opposite directions of air/gas flow including a plurality of bends at periodic positions along the pathway, an opening at one end of the pathway for communication with an exterior environment, an opening at the other end of the pathway for communication with a sterile environment, and a plurality of individual pockets located at at least some of the plurality of bends along the pathway and in at least one direction of air/gas flow along the pathway from the one end to the other end and with the individual pockets providing for trapping any bacteria introduced into the pathway at the one end and with all of such bacteria trapped before the other end of the pathway.

8. The devious path bacterial barrier of claim 7 wherein the elongated pathway is formed within a flat member and along the plane in which the flat member lies.

9. The devious path bacterial barrier of claim 8 wherein the flat member is formed from two portions each having a part of the pathway formed as a groove in one surface and with the surfaces contiguous and with at least a portion of each groove overlying the other to provide a continuous pathway between the grooves in each portion.

10. The devious path bacterial barrier of claim 9 wherein the two portions including the grooves are substantially identical and with one portion rotated relative to the other to form the continuous pathway.

11. The devious path bacterial barrier of claim 8 for use with a wall portion wherein the flat member is formed from a single portion having a groove in one surface and with the surface contiguous with the wall portion to provide the continuous pathway along the groove.

12. The devious path bacterial barrier of claim 7 wherein the pockets are located at the bends in both directions of air/gas flow along the pathway.

13. A devious path bacterial barrier for providing an air/gas pathway into and out of a sterile environment from an external environment, including a flat member lying within a plane and having spaced openings extending into the flat member and with one of the openings for communicating with the exterior environment and with the other of the openings for communicating with the sterile environment, a pathway extending between the openings and with the pathway extending within the flat member and alon g the plane to the flat member for interconnecting the opening and providing an air/gas pathway for both directions of air/gas flow between the one opening of the flat member and the other opening, and the pathway including a plurality of bends along its length and with each bend providing an area to trap any bacteria introduced into the pathway from the exterior environment communicating with the one opening and with all the bacteria trapped at a distance along the pathway before the other opening communicating with the sterile environment.

14. The devious path bacterial barrier of claim 13 additionally including individual pockets located at at least some of the bends and with the pockets extending in at least one direction of air/gas flow along the pathway.

15. The devious path bacterial barrier of claim 14 wherein the pockets are located at the bends in both directions of air/gas flow along the pathway.

16. The devious path bacterial barrier of claim 13 wherein the flat member is formed from two portions each having a part of the pathway formed as a groove in one surface and with the surfaces contiguous and with at least a portion of each groove overlying the other to provide a continuous pathway between the grooves in each portion.

17. The devious path bacterial barrier of claim 16 wherein the two portions including the grooves are substantially identical and with one portion rotated relative to the other to form the continuous pathway.

18. The devious path bacterial barrier of claim 13 for use with a wall portion wherein the flat member is formed from a single portion having a groove in one surface and with the surface contiguous with the wall portion to provide the continuous pathway along the groove.

19. A sterile package including a devious path bacterial barrier for providing an air/gas pathway into and out of the interior of the package from the exterior of the package, including
- a wall portion,
- an aperture in the wall portion of the package for communicating with the interior of the package,
- a flat member lying within a plane and having spaced openings extending into the flat member and with one of the openings for communicating with the exterior and with the other of the openings for communicating with the aperture in the wall portion of the package,
- a pathway extending between the openings and with the pathway extending within the flat member and along the plane of the flat member for interconnecting the openings and providing an air/gas pathway for both directions of air/gas flow between the one opening of the flat member and the other opening, and
- the pathway including a plurality of bends along its length and with each bend providing an area to trap any bacteria introduced into the pathway from the exterior to the one opening and with all the bacteria trapped at a distance along the pathway before the other opening commuunciating with the aperture.

20. The sterile package of claim 19 additionally including individual pockets located at at least some of the bends and with the pockets extending in at least one direction of air/gas flow along the pathway.

21. The sterile package of claim 20 wherein the pockets are located at the bends in both directions of air/gas flow along the pathway.

22. The sterile package of claim 19 wherein the flat member is formed from two portions each having a part of the pathway formed as a groove in one surface and with the surfaces contiguous and with at least a portion of each groove overlying the other to provide a continuous pathway between the grooves in each portion.

23. The sterile package of claim 22 wherein the two portions including the grooves are substantially identical and with one portion rotated relative to the other to form the continuous pathway.

24. The sterile package of claim 19 wherein the flat member is formed from a single portion having a groove in one surface and with the surface contiguous with the wall of the package to provide the continuous pathway.

* * * * *